United States Patent [19]

Wiethaup

[11] 4,400,972
[45] Aug. 30, 1983

[54] APPARATUS FOR DETERMINING THE FLOW BEHAVIOR OF A SMOKABLE ARTICLE

[75] Inventor: Wolfgang Wiethaup, Hamburg, Fed. Rep. of Germany

[73] Assignee: B.A.T., Cigaretten-Fabriken GmbH, Hamburg, Fed. Rep. of Germany

[21] Appl. No.: 227,705

[22] Filed: Jan. 23, 1981

[30] Foreign Application Priority Data

Jan. 23, 1980 [DE] Fed. Rep. of Germany ....... 3002244

[51] Int. Cl.³ .......................................... G01N 15/08
[52] U.S. Cl. ..................................................... 73/38
[58] Field of Search ............................................ 73/38

[56] References Cited

U.S. PATENT DOCUMENTS

| 3,115,767 | 12/1963 | Tyrrell et al. | 73/38 |
| 4,127,025 | 11/1978 | Mills et al. | 73/38 |
| 4,171,635 | 10/1979 | Calleson et al. | 73/38 |

FOREIGN PATENT DOCUMENTS 1025173 2/1958 Fed. Rep. of Germany ......... 73/38
2650058 5/1977 Fed. Rep. of Germany .

Primary Examiner—Steven L. Stephan
Assistant Examiner—Joseph W. Roskos
Attorney, Agent, or Firm—Armstrong, Nikaido, Marmelstein & Kubovcik

[57] ABSTRACT

An apparatus for determining the flow characteristics of a smokable article is provided. The apparatus comprises a smoking machine and a holding device coupled to the smoking machine for holding a smokable article. An air-tight chamber is movably mounted on the holding device for enclosing at least a portion of the smokable article. Flow characteristic measuring devices are coupled to the holding device for measuring the flow characteristics of a gas flowing through the smokable article.

18 Claims, 3 Drawing Figures

APPARATUS FOR DETERMINING THE FLOW BEHAVIOR OF A SMOKABLE ARTICLE

BACKGROUND OF THE INVENTION

The invention relates to an apparatus for determining the flow behavior of a smokable article, such as cigars, cigarillos and especially cigarettes. The problems significant herein to smokable articles shall be discussed in relation to cigarettes.

DESCRIPTION OF THE PRIOR ART

The flow resistance, the type of ventilation and the magnitude of the ventilation are essential design parameters for the concept of flow behavior of a cigarette. The "ventilation flow" is denoted as the air flow entering the cigarette elsewhere than through the incandescence zone. The degree of ventilation is the portion of the ventilation flow in the total flow issuing from the mouthpiece.

A partial vacuum occurs in the cigarette during an inhaling draw, whereby a ventilation flow passes through the air-permeable cigarette paper into the strand of tobacco, this being the so-called strand ventilation and, if a filter is present, through the filter, this being the so-called filter ventilation.

The ventilation causes a drop in the yield of all smoke ingredients, so that if the ventilation is accurately known, in particular if there is precise knowledge of the relations between the strand ventilation and the filter ventilation, the smoke yield may be optimized.

Basic research is available and known for the non-burning cigarette, dealing with the optimal design for strand and filter ventilations. As regards quality control, the flow resistance and selectively the degrees of filter, strand and total ventilations are continuously monitored during cigarette manufacture.

Conventional test equipment suffers from the drawback that selectively only one of the flow resistance or the ventilation flow, i.e., the degree of ventilation, may be determined. It is not possible to measure both values using one and the same apparatus.

Moreover the draw resistance and the ventilation flow can only be measured along an accurately defined length of the cigarette—for instance it is impossible to determine the ventilation flows and the flow resistance over segments of different lengths of a cigarette.

SUMMARY OF THE INVENTION

It is therefore the object of the invention to create an apparatus for determining the flow behavior of a smokable cigarette, the apparatus being free of the above mentioned drawbacks.

In particular, the invention proposes an apparatus for permitting the measurement of the ventilation flows in the areas of different lengths of the smokable article, for instance a cigarette, and if need be also on a burning smokable article.

The advantages obtained from the invention rest on the following operation: an air-tight chamber at least partially surrounding the cigarette can be moved on a holding means holding the cigarette. The part of the cigarette surrounded by the chamber is therefore accurately defined, so that the flow sucked through this part in the course of one draw is precisely defined and hence the ventilation flow and if desired, the degree of ventilation of this region may also be measured.

If the chamber surrounds less than the whole cigarette, then obviously that part exposed to the atmosphere must be accounted for.

This apparatus also permits testing burning cigarettes, as the chamber surrounds the cigarette as far as a zone closely behind the incandescence area. As the incandescence area progresses, the chamber is gradually displaced accordingly.

To distinguish between the strand ventilation and the filter ventilation, a further air-tight chamber mounted on said holding means may be provided, which also is connected to a flow measuring means. In this case, the displaceable chamber will surround only the strand, and therefore is hereafter termed the strand chamber, while the other stationary one, termed "filter chamber" surrounds only the filter.

In order to have the capability to simultaneously measure the flow resistance a pressure pickup is connected between the holding means and the smoking machine, which measures the differential pressure between the connection, in general the mouthpiece side end of the cigarette, and a given other reference point for the cigarette. Suitable reference points are (1) the ambient air pressure, by means of which one obtains the flow resistance of the cigarette; (2) the connection to the strand ventilating air, by means of which the pressure drop across the strand paper, the strand and filter if any is measured; or (3) the connection to the filter ventilation; by means of which the flow resistance is obtained from the filter ventilation zone and the filter material.

For reasons of compactness and to simplify the feed lines, both the ventilating air for the filter ventilation and the ventilating air for the strand ventilation should be located at the end of the apparatus which is on the side of the smoking machine.

Whereas research already exists about non-burning cigarettes, as mentioned above, there has been so far only a small amount of ventilation on the flow resistance and the magnitude of the strand and filter ventilation when smoking a cigarette by drawing on it, that is, for non-stationary processes. Either the flow resistance or the filter ventilation was measured; in another approach, the effect of the flow resistance of the generally conical incandescence zone of the non-burning cigarette was simulated, i.e., ascertained indirectly.

In the non-stationary case, that is when smoking a burning cigarette by drawing on it, in order to also ascertain the flow resistance, the kind of ventilation and the magnitude of ventilation, a preferred embodiment of the invention provides that the displaceable chamber be moved along with the incandescence zone. Thus, the displaceable chamber—which permits for instance measuring the strand ventilation—is moved along in accordance with the motion of the incandescence zone, whereby the measurement automatically takes into account the shortening of the strand length and thus the above listed parameters can be measured and recorded during all of the smoking.

As already mentioned above, strand and filter ventilations can be distinguished by using another stationary chamber, so that very accurate conclusions are possible about the essential design data of a cigarette.

In a preferred embodiment, the displaceable chamber is moved in accordance with the incandescence zone by means of a sensor responding to the radiation of this incandescence zone, in particular a photo-diode. An electric circuit is provided, which permits a very precise control of this in-step motion.

The strand chamber must be kept fixed during drawing because the flow measurements are carried out in this time interval. This secondary condition is easily observed by aiming the photodiode on a point in the incandescence zone wherein the temperature distribution changes only slightly during the draw. Experimentation has shown that the temperature of the incandescence zone remains adequately constant at some distance from the paper burning line, i.e., this area can be used for the aiming of the photodiode.

Appropriately the holding means, the filter chamber and the strand chamber are formed by mutually concentric tubes, resulting in a very compact design with very low dead volumes and very small inherent resistances. The complete assembly can be taken apart to clean the individual components, as the individual tubes are only connected by seals. By a suitable selection of the dimensions of the tubes and the seals used, the apparatus can be adapted to various cigarette or filter sizes.

BRIEF DESCRIPTION OF THE DRAWINGS

The invention is further explained below in relation to illustrative embodiments and the schematic drawings.

DETAILED DESCRIPTION OF THE PREFERRED EMBODIMENT

Figure 1:
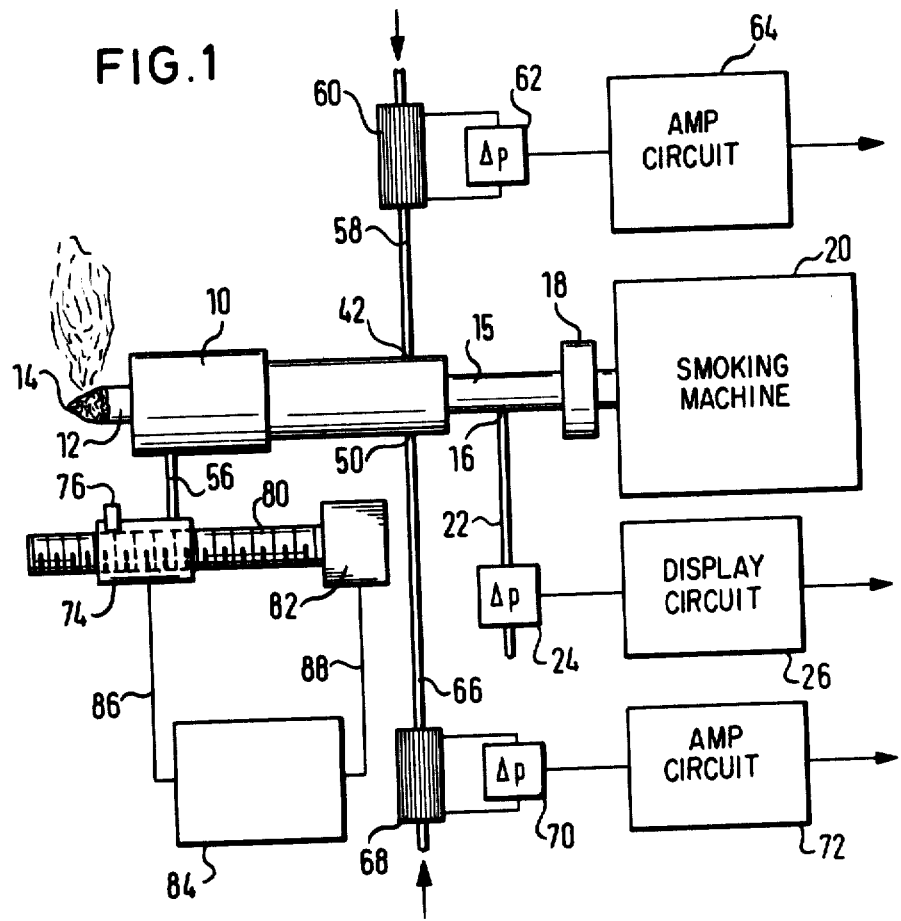
FIG. 1 is an overall view of the preferred embodiment of the present invention to determine the flow behavior of a smokable article.

As seen in FIG. 1, a burning cigarette 12 with an incandescence zone 14 is seated in a holding means 15 onto which is slipped a ventilation testing head 10. The holding means 15 is connected by a Cambridge filter 18 to a conventional smoking machine.

The holding means 15 is provided with an exhaust 16 connected to a pressure pickup 24. The electric signal generated by the pressure pickup 24 is amplified by circuit 26 that also stores the maximally occurring pressure difference. The circuit 26 displays as its measured value the flow resistance, as further discussed below.

Figure 2:
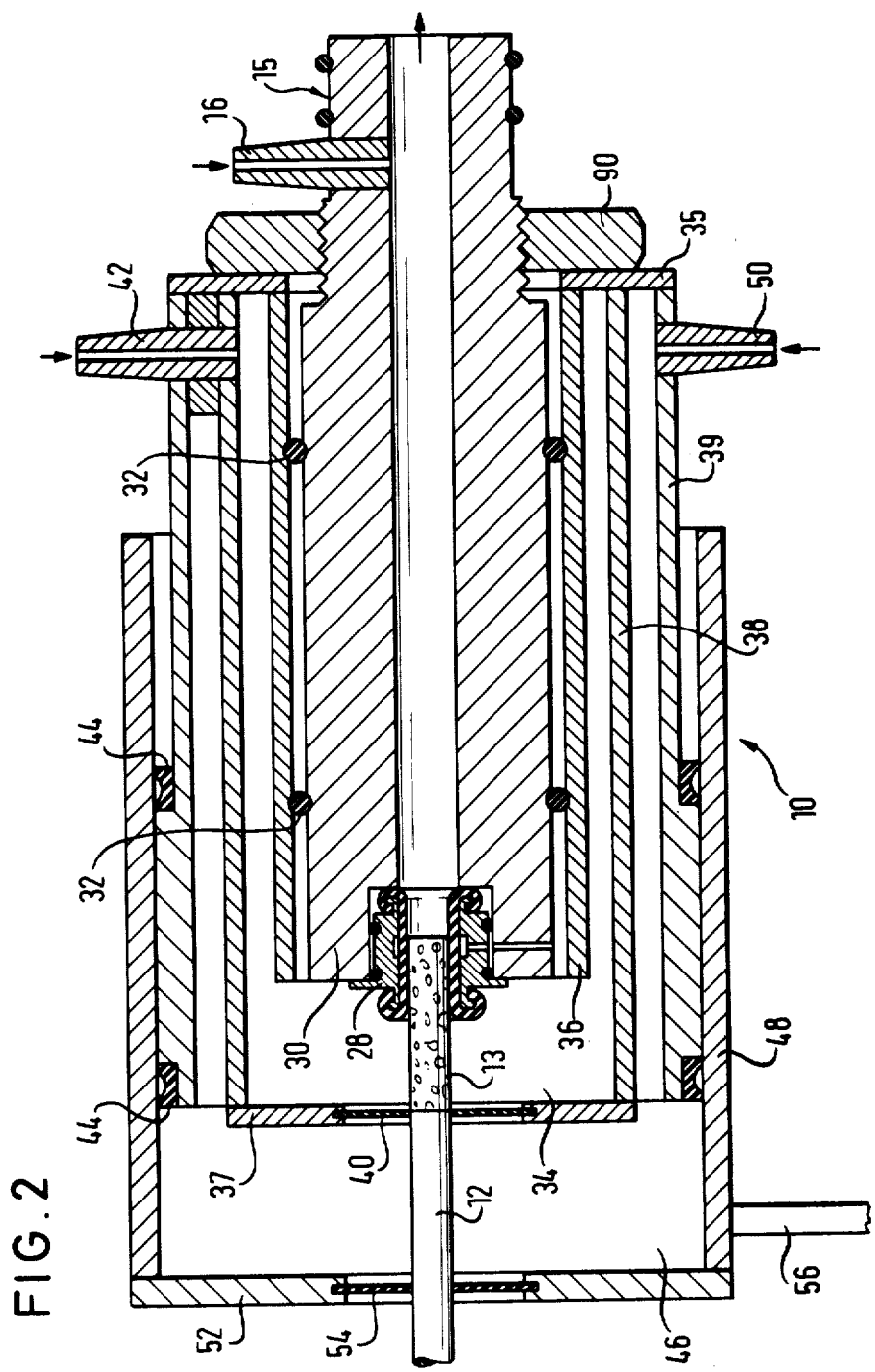
FIG. 2 is a cross-section of the ventilation testing head.

As shown in detail in FIG. 2, the ventilation testing head is provided with a holding means 15 consisting of a cylindrical tube 30 coupled on one side to the smoking machine 20. The holding means 15 holds the cigarette in an airtight manner on the other side by means of a Borgwaldt cigarette holder.

A pressure test connector 16 is provided at the end of the holding means 15 facing the smoking machine 20. Part of the air sucked in by the smoking machine 20 flows from the outside through said connector 16. The air discharged from the pressure test connector 16 is fed through line 22 to the pressure pickup 24.

Three mutually concentric tubes, namely an inside tube 36 resting on the outside of the tube 30, a center tube 38 and an outer tube 39 are slipped over the tubular holding means 15.

The three tubes 36, 38, 39 are sealed as shown in FIG. 2 on the right hand side by an end surface 35 while, as shown in FIG. 2, only the end rim portion of the center tube 38 is sealed by a disk 37. The disk 37 comprises a circular aperture through which passes the cigarette. An elastic tetrafluoroethylene sealing washer 40 is placed between the inside rims of the circular aperture of the end disk 37 and the cigarette.

The space enclosed between the end disk 37, the elastic sealing washer 40, the center tube 38 and the inside tube 36 and also the inside of the right-hand end plate 35 defines the "filter chamber", as it contains only the filter 13 of the cigarette. The transition from filter to tobacco strand therefore takes place approximately at the location of the elastic sealing washer 40.

O-rings 32 are provided between the outer surface of the tubular support 30 and the inside surface of the inside tube 36, whereby this region is sealed against the outside.

The filter chamber 34, that is the area between the center tube 38 and the inner tube 36, is provided with an intake connector 42 at the smoking-machine side, for admitting the filter ventilating air.

As shown by FIG. 1, the ventilating air is fed through a line 58 to the intake connector 42; line 58 is connected to a laminar flow element 60. The pressure drop across this laminar flow element 60 is measured by a differential pressure pickup 62, and amplified and integrated by the circuit 64 which produces and output indicative of the volume of the filter ventilation flow.

The annular spaces between the center tube 38 and the outer tube 39 are open to the left side, as shown in FIG. 2 and, therefore communicate with the strand of the cigarette 12.

A further tube 48 is slipped onto the tube 39 and, as shown in FIG. 2, is closed on the left side by an end plate 52. This end plate 52 also comprises a circular aperture into which is set an elastic polytetrafluoroethylene sealing washer 54 to seal the region between the inside rim of the aperture and the cigarette.

The sealing between the tube 48 and the outer tube 39 is implemented by polytetrafluoroethylene washers 44 which offer both a good sealing effect and good sliding properties.

The space between the two end surfaces 52 and 37 and between the center tube 38 and the outer tube 39 or 48 defines the "strand chamber" and comprises an intake* connector 50 which communicates through a line 66 with a further laminar flow element 68 (FIG. 1). In this case too the pressure drop across the laminar flow element is ascertained by a differential pressure pickup 70, so that the strand ventilation flow is computed in a circuit 72 containing an amplifier and integrator and is displayed by same as the test value output thereto.

*presumably due to typographical error, the German words for intake and exhaust being close, the German text at this passage actually states "exhaust" which is unlikely in relation to FIG. 2; moreover, the German claim 1 uses "intake" in relation to component 40.

By using polytetrafluoroethylene elastic seals of different sizes and different cigarette holding means, it is furthermore possible to test also smokable articles with varying diameters. Moreover test samples of different lengths, both as regards filters and strands, can be investigated as the axial lengths of the filter and strand chambers can be varied independently.

A threaded nut 90 is located at the end of the tube 30 which is near the smoking machine and this nut 90 is used to tighten the tube 30 and simultaneously acts as an adjustable stop means for the filter chamber motion to the right as shown in FIG. 2.

A drive means 56 rigidly fixed in a support 74 for a photodiode 76 is mounted to the tube 48 of the strand chamber 46. This photodiode 76 is aimed at a point of the conical incandescence zone 14 of the cigarette 12 and appropriately onto a location somewhat in front of the paper burning line, as the temperature distribution of this area does not excessively change during one draw.

The support 74 of the photodiode 76 moves on a threaded shaft 80 that may be driven by a motor 82. The output signal from the photodiode 76 is fed though a line 86 to a control circuit 84 which in turn actuates through line 88 the motor 82.

Thus the control circuit 84 so adjusts by means of the electric motor 82, the threaded shaft 80 such that the photodiode 76 is always carried in step with the motion of the incandescence zone 14 and so that also the tube 48 of the filter chamber 46 moves along correspondingly. In this manner, the filter chamber 46 is moved to the right in FIG. 2, whereby the ventilation and the outflow resistance of the particular remaining strand and additionally the ventilation of the filter 13 can be measured during smoking by drawing.

Figure 3:
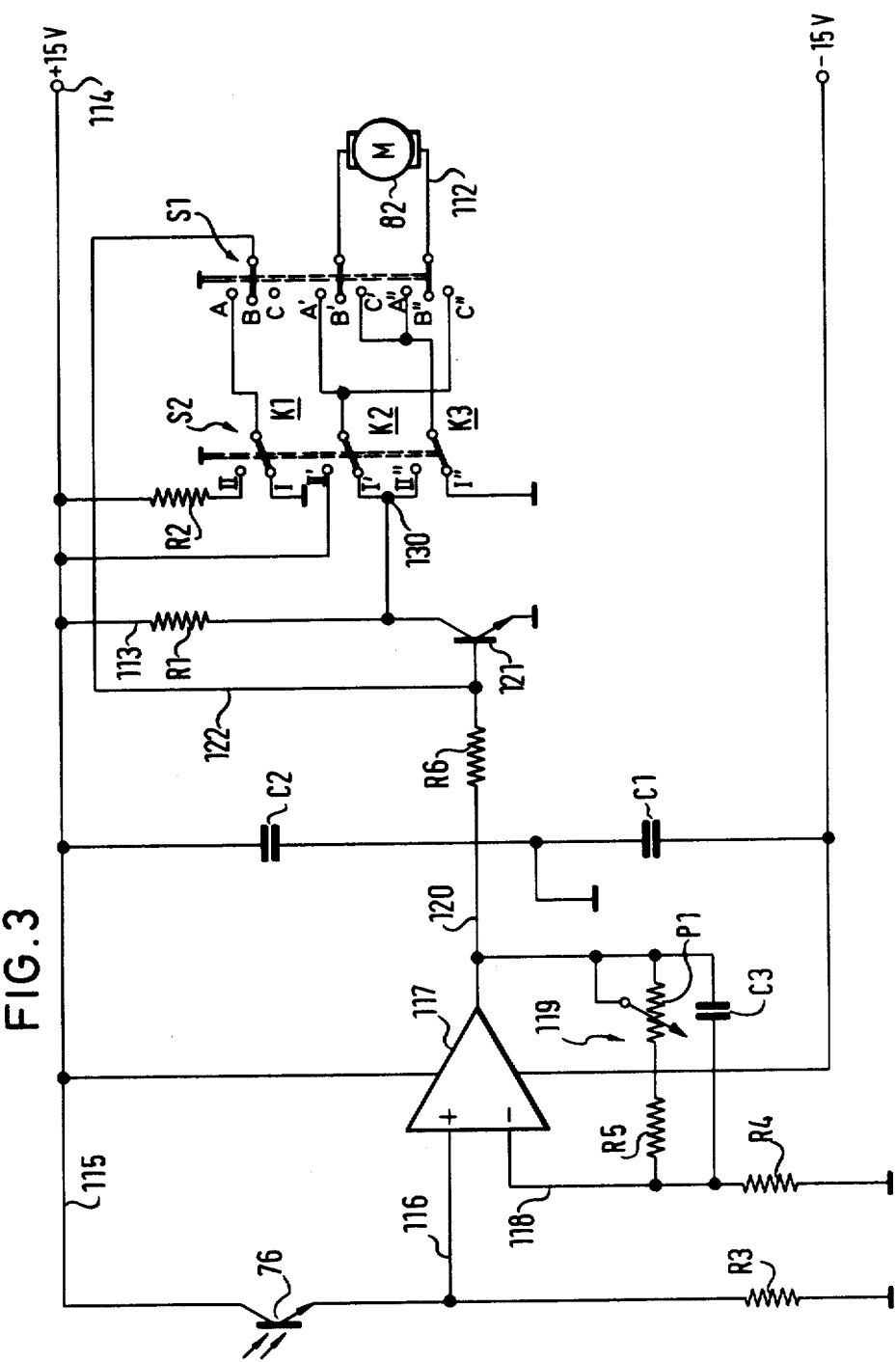
FIG. 3 is a circuit diagram of the electric portion of the apparatus.

The electrical control of the motor will be now discussed in relation to FIG. 3.

The circuit of motor 82 includes a switch S1, by means of which the rotation of the motor can be reversed or its motion stopped. This switch S1 comprises three poles, respectively capable of of making contact with three stationary terminals denoted by A,B,C; A',B',C'; A",B",C".

When the poles make contact as shown in FIG. 3 with the lower terminals C,C' and C", the motor 82 is switched on and rotates in its forward direction, whereby as shown in FIG. 1, the photodiode 76 moves from left to right on the threaded shaft 80.

When the poles make contact with the center contacts B, B' and B" of FIG. 3, the motor 82 is switched off, and the threaded shaft 80 does not rotate.

When lastly the poles make contact with the upper stationary terminals A, A' and A", the direction of rotation of the motor 82 is reversed, that is, the photodiode 76 in FIG. 1 is moved back from the right hand side into the left side initial position at the tip of the cigarette 12.

A further switch S2 is connected to switch S1 to set the basic mode of operation of the apparatus in a manner yet to be discussed.

In particular, a junction point of the two stationary terminals A' and C" of the switch S1 is connected to a first pole K2 of the switch S2, while a junction point of the two fixed terminals C' and A" of the switch S1 is connected to a second pole K3 of the switch S2. Lastly the terminal A of the switch S1 is connected to a third pole K1 of the switch S2.

The upper pole K1 of the switch S2 connected to the fixed terminal A as shown in FIG. 3 can be reversed from a switch position I, when it is grounded, to switch position II, in which it is connected through a resistance R2 to the positive terminal of a voltage source 114.

The center terminal K2 shown in FIG. 3 can be moved between a switch position I' and a switch position II' in which it makes direct contact with the positive terminal of the voltage source 114.

The lower pole K3 of the switch S2 shown in FIG. 3 finally can be moved between a switch position I" where it is grounded and a switch position II".

The two switch positions I' and I" are connected by a common junction 130 which in turn is connected through a resistance R1 and a line 113 to the positive terminal of the voltage source 114 and through the collector-emitter path of the transistor 121 to ground. The base of the transistor 121 is connected by line 122 to the upper pole of the switch S1. The other two poles of the switch S1 are connected to the motor 82.

The photodiode 76 is connected by one terminal through a resistance R3 to ground and by the other terminal through a line 115 to the positive terminal of the voltage source 114.

A line 116 from the junction of the resistance R3 and the photodiode 76 is connected to the comparator 117, which receives at its (+) input the output signal from the photodiode 76 and its (−) input, through a line 118, a reference potential, the amplitude of which can be varied. The setting of the reference potential takes place in a feedback circuit 119 containing the resistance R4 and R5, a capacitor C3 and potentiometer P1. The potentiometer P1 adjusts the reference potential. The output from the comparator 117 is connected through a further resistance R6 and a line 120 to the base of the transistor 121.

The negative terminal of the 15 v power supply is connected through two capacitors C1 and C2 to the positive terminal, as shown in FIG. 3.

For the lower position of the switch S2 that is shown, the terminal I' is connected through the line 113 and the resistance R1 to the positive terminal of the voltage source 114, while the terminal I" is at ground.

The functioning of the electric control circuit will now be explained. After the cigarette 12 has been placed in the holding means 15 and same has been connected to the smoking machine 20, the cigarette 12 is lit and smoked. Thereupon the photodiode 76 is moved back to the left end of the threaded shaft 80 as shown in FIG. 1 by so setting the switch S1 that its poles contact the terminals A, A' and A". Once the left side end has been reached, the switch S1 is reversed that its poles contact the terminals C, C' and C", the motor 82 thus rotates in its forward direction and the photodiode 76 moves to the right as shown in FIG. 1. This motion of the photodiode 76 is coupled to the rate of displacement of the incandescence zone 14 of the cigarette 12 in such a manner that it will take place according to said incandescence zone displacement. The fixation of the photodiode 76 onto the incadescence zone 14 of the cigarette 12 can be implemented as a function of the position of the switch S2 in the following two modes:

If the switch S1 is in the operating position and the poles of the second switch S2 rest against the stationary terminals I, I' and I", as shown in FIG. 3, the current passes from the positive terminal of the voltage source 114 through the resistance R1, the terminals I', C", the motor 82 and the terminals C' and II", whereby the motor 82 rotates and the photodiode 76 is displaced on the threaded shaft 80. If now the photodiode 76 arrives at a location where it receives a precisely defined radiation intensity from the incandescence zone 14 of the cigarette 12, then the photodiode 76 becomes conducting, that is, hard-driving. Current then passes through the photodiode 76, and this be compared in comparator 117 with a reference value, the comparator 117 generating in the case of equality, an output signal that is applied to the base of the transistor 121 which turns it on and renders it hard-driving, whereby the current from the line 113 no longer passes through the motor 82, but rather directly through the transistor 121, and hence the motor 121 is stopped. This means accordingly that the photodiode 76 no longer is displaced on the threaded shaft 80, and therefore the photodiode 76 is fixed onto the incandescence zone 14 of the cigarette 12. Only after the generally conical incandescence zone 14 of the cigarette 12 has moved out of the photodiode response range will transistor 121 be turned off as blocked again and hence the motor 82 will be started again. Seen from the tip of the incandescence zone 14, the photodiode 76 therefore is made to follow, in this mode of operation.

When setting the switch S2 on the stationary terminals II, II' and II", whereby the terminals II' and II" are connected through the electric motor 82, no current will be present if the photodiode 76 is non-conducting. Correspondingly, the motor 82 does not rotate, and the photodiode 76 remains stationary.

It is only when the incandescence zone 14 of the cigarette 12 approaches the response range of the photodiode 76 that photodiode becomes conducting and hard-driving, whereby in the manner explained above a signal is applied to the base of the transistor 121, which then also becomes hard-driving and hence actuates the motor 82 and the advance of the threaded shaft 80. In this mode of operation therefore the photodiode 76 is displaced in front of the incandesence zone 14 in the direction of the mouthpiece, that is toward the filter 13.

To permit defect-free reverse motion of the motor 82 when the switch S2 is in the II position, the transistor 121 will have to be on. To that end, the feedback line 122 connected through the terminals II and A to the positive terminal of the voltage source 114 is provided, which is also connected to the base of the transistor 121.

The response range of the photodiode, that is the radiation intensity at which the photodiode 76 responds, can be set by means of the potentionmeter P1.

As the photodiode 76 is carried along from left to right in FIG. 1 according to the motion of the incandescence zone 14 of the cigarette 12. The tube 48 of the strand chamber 46 of FIG. 2 also is displaced to the right on the outer tube 39 of the filter chamber 34. Thereby the conical incandescence zone 14 always remains outside the ventilation testing head 10, while the particular residual cigarette strand is sealed airtight with respect to the ambient atmosphere from an area closely behind the incandescence zone 14 (FIG. 1) to the beginning of the filter 13. The filter 13 of the cigarette 12 also is sealed tight with respect to the ambient atmosphere in the filter chamber 34, where it is apart from the strand.

As the two flow sensing means 60, 62, 64 and 68, 70,72 measure the filter ventilating flow and the strand ventilating flow respectively, the ventilation degree of the filter ventilation and of the strand ventilation respectively can be determined from the known constrained volume flow of the smoking machine.

The pressure-measuring connector 16 at the holding means 15 of the ventilating testing head 10 is used to measure the flow resistance. The pressure differential pickup 24,26 can measure in this process the pressure difference between the pressure measuring connector and another specified reference point of the cigarette. This other, specific reference point may be (a) the ambient air pressure, whereby the flow resistance of the cigarette 12, the so-called "open draw resistance" is obtained;

(b) the intake 50 for the strand ventilating air, whereby the pressure drop across the strand paper, the strand and the filter 13 is obtained, and (c) the intake 42 for the filter ventilating air, whereby the pressure drop and hence the flow resistance of the filter ventilation zone and the filter material is obtained.

As the processes involving pressure cannot be held stationary, the maximum pressure difference that occurs must be detected in suitable manner, stored and taken into account in the computational analysis.

What is claimed:

1. An apparatus for determining the flow characteristics of a smokable article said apparatus comprising:
   (a) a smoking machine;
   (b) holding means, coupled to said smoking machine, for holding said smokable article;
   (c) air-tight enclosed chamber means, movably mounted on said holding means, for enclosing at least a portion of said smokable article, said chamber means including a first chamber for enclosing a strand portion of the smokable article, a secod chamber for enclosing a filter portion of the smokable article, a first gas intake means coupled to said first chamber and a second gas intake means coupled to said second chamber; and
   (d) flow characteristic measuring means, coupled to said holding means, for measuring the flow characteristics of gas from said gas intake means through said smokable article.

2. An apparatus for determining the flow characteristics of a smokable article as set forth in claim 1 including seal means positioned between said holding means and said chamber means.

3. An apparatus for determining the flow characteristics of a smokable article as set forth in claim 2, wherein said seal means is an O-ring.

4. An apparatus for determining the flow characteristics of a smokable article as set forth in claim 1, including a first elastic sealing washer means positioned between said chamber means and the strand portion of said smokable article.

5. An apparatus for determining the flow characteristics of a smokable article as set forth in claim 4, including a second elastic sealing washer means positioned between said first and second chambers.

6. An apparatus for determining the characteristics of a smokable article as set forth in claim 5, wherein said first and second sealing washer means comprise polytetrafluoroethylene.

7. An apparatus for determining the characteristics of a smokable article as set forth in claim 5, wherein said first sealing washer means is positioned between said first chamber and said smokable article.

8. An apparatus for determining the characteristics of a smokable article as set forth in claim 1, wherein said flow characteristic measuring means is a pressure measuring means for measuring the pressure of gas which has flowed from said chamber means through said smokable article.

9. An apparatus for determining the flow characteristics of a smokable article as set forth in any one of claims 1 or 8, wherein said holder means comprises a Borgwaldt holder and a tube connected thereto.

10. An apparatus for determining the flow characteristics of a smokable article as set forth in any of claim 1, wherein the enclosed portion of said smokable article does not include the incandescence zone thereof.

11. An apparatus for determining the flow characteristics of a smokable article as set forth in claim 10, including moving means for moving said chamber means as a function of the movement of said incandescence zone.

12. An apparatus for determining the flow characteristics of a smokable article as set forth in claim 11, wherein said moving means includes sensor means for sensing said incandescence zone.

13. An apparatus for determining the flow characteristics of a smokable article said apparatus comprising:
   (a) a smoking machine;
   (b) holding means, coupled to said smoking machine, for holding said smokable article;
   (c) air-tight enclosed chamber means, movably mounted on said holding means, for enclosing at least a portion of said smokable article not including the incandescence zone thereof, said chamber means including at least one gas intake means, sensor means for sensing said incandescence zone, and moving means coupled to said sensor means for moving said chamber means as a function of the movement of said incandescence zone; and
   (d) flow characteristic measuring means, coupled to said holding means, for measuring the flow characteristics of gas from said gas intake means through said smokable article.

14. An apparatus for determining the flow characteristics of a smokable article as set forth in any one of claims 12 or 13, wherein said sensor means is rigidly coupled to said chamber means and wherein said moving means includes drive means coupled to sensor means for moving said sensor means and thereby said chamber means, in accordance with the detection of said incandescence zone by said sensor means.

15. An apparatus for determining the flow characteristics of a smokable article as set forth in claim 14, wherein said sensor means is a photodiode having an on state and an off state, and wherein said moving means includes control circuit means for coupling said sensor means to said drive means, wherein said control circuit operates said drive means in response to the state of said photodiode means.

16. An apparatus for determining the flow characteristics of a smokable article as set forth in claim 15, wherein said control circuit means includes switch mmeans, for activating and deactivating said drive means.

17. An apparatus for determining the flow characteristics of a smokable article as set forth in claim 16, wherein said switch means is a transistor.

18. An apparatus for determining the flow characteristics of a smokable article as set forth in claim 17, wherein said control circuit means includes directional switching means for controlling the direction of motion of said drive means and thereby the direction of movement of said sensor means and said chamber means.

* * * * *